United States Patent [19]

Ontek

[11] Patent Number: 4,561,315
[45] Date of Patent: Dec. 31, 1985

[54] LIQUID SAMPLING APPARATUS AND METHOD OF MANUFACTURE THEREFOR

[76] Inventor: Louis Ontek, RD #3, Box 365, Jackson, N.J. 08527

[21] Appl. No.: 464,589

[22] Filed: Feb. 7, 1983

[51] Int. Cl.⁴ ............................................. G01N 1/12
[52] U.S. Cl. ................................................. 73/864.64
[58] Field of Search ........... 73/864.63, 864.64, 864.65, 73/864.66, 864.67; 33/126.4 R; 137/533.11; 294/69 R

[56] References Cited

U.S. PATENT DOCUMENTS

| | | | |
|---|---|---|---|
| 2,509,629 | 11/1936 | Erwin et al. | 166/167 |
| 3,620,228 | 11/1971 | Schmid | 137/533.11 |
| 4,082,483 | 4/1978 | Sprenger | 294/69 R |
| 4,155,374 | 5/1979 | Diehl | 137/519.5 |
| 4,305,279 | 12/1981 | Onter | 73/864.63 |

*Primary Examiner*—S. Clement Swisher
*Attorney, Agent, or Firm*—Sachs & Sachs

[57] ABSTRACT

A liquid sampling apparatus for use in sampling the liquid in a well pipe to determine surface contaminants contained therein includes a unitary tubular housing formed to provide a valve seat therein. A ball, freely movable within the tube, is inserted to cooperate with the valve seat to form a valve which remains closed once the sampling tube is filled with water. The opposite end includes a retaining device onto which is affixed a flexible line that has its opposite end affixed to the removable well cap. The flexible line is used to remove the liquid sampling apparatus from the well after a sample of the liquid contained therein has been obtained.

8 Claims, 4 Drawing Figures

LIQUID SAMPLING APPARATUS AND METHOD OF MANUFACTURE THEREFOR

BACKGROUND OF THE INVENTION

1. Field of the Invention

The present invention relates to liquid sampling devices, and in particular, to a liquid samping apparatus which may be used to obtain samples of contaminants appearing on the surface of well water and directly beneath the surface thereof.

2. Discussion of the Relevant Art

The art abounds with devices which are used to sample liquids to determine the density, amount of contamination, etc. Generally, these devices disclose a valve which is sealed by the weight of the liquid sample contained in the container. Typical of the sampling devices which utilize a ball valve is U.S. Pat. No. 1,511,591 issued to Colligan on Oct. 14, 1924. The device disclosed therein is a liquid samplng apparatus that includes a plurality of tubular sections with the immersible end thereof being provided with a restricted portion which is sealed by the use of a spherical weight that is held by a pin above the level of the liquid to be sampled and, upon removal of the pin, is permitted to seal the restricted opening upon withdrawal of the sampling device.

Another device which utilizes a ball-type valve is disclosed in U.S. Pat. No 4,050,315 issued to Markfelt on Sept. 27, 1977. The apparatus disclosed therein is suitable for taking liquid samples in a well at any desired level under the surface and includes a body having a bullet-nosed weighted lower end in order to help avoid disturbing the surface of the water in the well as it is applied thereto. The apparatus requires that the lowering cable be jerked when the sampling device reaches the level at which a sample is to be obtained. By utilizing a pair of ball valves the fluid is permitted to enter the sampling chamber wherein a second ball floats to the surface within the chamber closing the inlet port thereby preventing contamination at higher levels from entering the sample chamber.

Generally, these devices are complicated mechanisms and require one or more movements of a string or contact with the bottom surface of the container for operation. The use of these devices on the surface of liquids would appear to disturb the liquids from which a sample is to be obtained thereby providing erroneous results by not including the liquids that may be floating on the surface from which the sample is to be taken. Moreover, the relatively simple devices discussed above may easily be rendered ineffective by dirt, or other particles which may enter the opening of the valve preventing the proper seating of the valve closing mechanisms. In addition, utilizing the sampling apparatus over long periods of time can cause particle buildup which again can prevent the sampling apparatus from operating properly.

SUMMARY OF THE INVENTION

The present invention overcomes shortcomings found in the prior art by providing a simple sampling apparatus which contains no surfaces, crevices or ledges, upon which dirt or particles can accumulate and prevent the proper operation of the ball valve.

Therefore, it is an object of the present invention to provide a relatively simply liquid sampling device that is reliable and easy to operate.

Another object of the present invention is to provide a liquid sampling device that is capable of obtaining a sample of liquid at the surface thereof, without disturbing any of the contaminants which may be floating thereon.

It is yet another object of the present invention to provide a liquid sampler which can sample liquid at any desired location below the surface of a well and which is easy to operate, easy to transport, economical to manufacture, and readily cleanable.

It is still another object of the present invention to provide a liquid sampling apparatus that is readily stored in a well pipe and is removably affixed to the well cap, thereby making it available whenever required.

Still another object of the present invention is to provide a liquid sampling apparatus that is simple to manufacture and is reliable by providing means for self-cleaning any particles out of valve portion during use.

It is still another object of the present invention to provide a liquid sampling apparatus that contains a minimum number of parts and overcomes shortcomings of devices known in the prior art.

Yet another object of the present invention is to provide a method of manufacturing a simple, reliable, readily manufacturable, sampling device that contains a minimum number of parts for operation.

A liquid sampling apparatus, according to the principles of the present invention, for use in a well pipe having a removable cap comprises a unitary elongated hollow housing means for insertion into a well pipe. The internal diameter of the well pipe is larger than the outer diameter of the hollow housing. The housing includes a retaining device disposed on one end for retaining one end of a flexible line thereon and includes a valve seat disposed proximate the other end of the housing. The valve seat is an integral part of the housing and extends inwardly. A spherical ball is disposed between the valve seat and the end of the housing onto which the retaining device is positioned. The ball moves freely within the housing and is adapted to cooperate with the valve seat to retain liquids disposed between the valve seat and the housing end having the retaining means affixed thereon. A restraining device is disposed within the housing to prevent the ball from falling out of the housing during transportation or when it is being filled with liquid.

A method of manufacturing a liquid sampling apparatus, according to the principles of the present invention, comprises the steps of, dipping a portion of a hollow tube of rigid plastic material into a bath having a temperature above the flow point of the material; inserting the material into a jig suitable for receiving the tubular material and having an open area for exposing a small portion of the heated material; placing a separable hourglass-like fixture member into the tubular material, the fixture having an outer diameter slightly smaller than the inner diameter of the tubular material, the narrow portion of the hourglass-like fixture member is disposed within the open area of the fixture; applying a flexible cord member about the circumference of the tubular member in line with the narrow portion of the hourglass-like fixture member with a holding bow; moving the bow back and forth perpendicular to axis of the tubular material until the tubular material cools to room temperature removing the separable hourglass-like fixture from the tubular member; inserting a spherical member into the tube at the end opposite the heated portion; placing a restraining device into the tubular material from the end opposite the heated portion; and forming a retaining device proximate the non-heated end of the tubular material.

The foregoing and other objects and advantages will appear from the description to follow. In the description, reference is made to the accompanying drawing which forms a part hereof, and in which is shown by way of illustration a specific embodiment in which the invention may be practiced. This embodiment will be described in sufficient detail to enable those skilled in the art to practice the invention, and it is to be understood that structural changes may be made without departing from the spirit and scope of the invention. The following detailed description is, therefore, not to be taken in a limiting sense, and the scope of the present invention is best defined by the appended claims.

BRIEF DESCRIPTION OF THE DRAWINGS

In order that the invention may be more fully understood, it will now be described, by way of example, with reference to the accompanying drawing wherein like reference characters refer to like elements.

DESCRIPTION OF THE PREFERRED EMBODIMENTS

Figure 1:
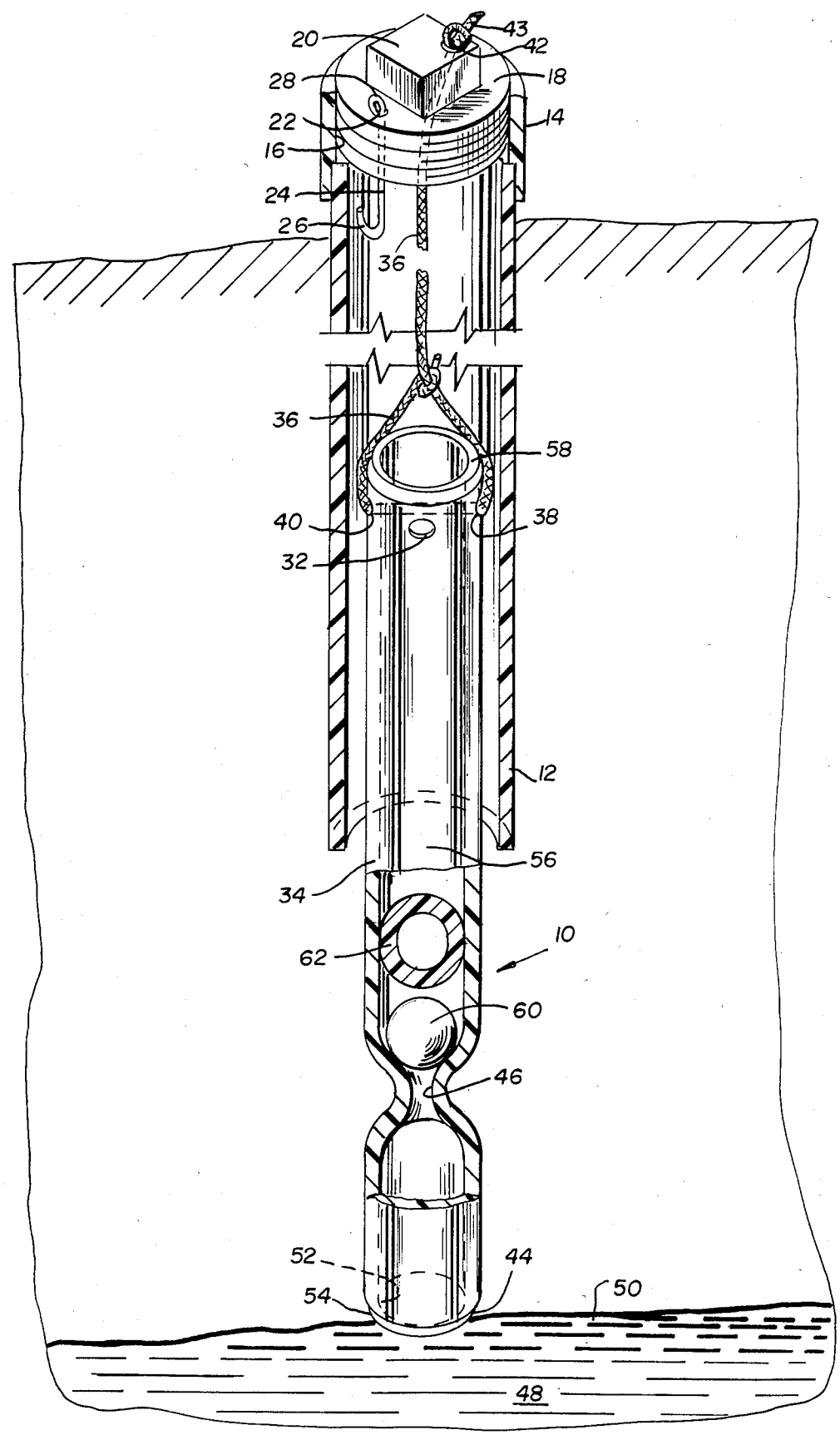
FIG. 1 is a pictorial representation of a well pipe embedded in the ground with a well cap thereon and a liquid sampling apparatus partially shown in cross-section, according to the principles of the present invention.

Referring now to the figures, and in particular to FIG. 1, wherein a liquid sampling apparatus 10 is shown positioned within a conventional well pipe fabricated from polyethylene, polyvinyl chloride, or any other suitable material. The well pipe sections may be connected together by means of couplers, not shown, and held by an adhesive such as acetone, in a conventional manner. The well pipe 12 is provided with a well topping 14 which is adhesively affixed to the well pipe 12 and retained thereon in a conventional manner. The well topping 14 is provided with interior threads 16 which are adapted to cooperate with the external threads provided on a well cap 18.

The well cap 18 is preferably provided with an extending portion 20 which is rectangular, as shown, or hexagonal in shape so that a wrench may be applied thereto for easy removal of the well cap from the well topping by an individual who is to use the liquid sampling apparatus 10. The well cap 18 is also provided with an aperture 22 proximate the circumference thereof. A retaining device 24, which in the preferred embodiment has a hooked portion 26 extending downwardly from the cap 18 into the well pipe 12 and a bent or rounded portion 28 which is larger than the aperture 22 thereby retaining the retaining device 24 in the cap 18.

The hooked shaped portion 26 of the retaining device 24 is adapted to cooperate with an aperture 32 provided on the housing 34 of the liquid sampling apparatus which preferably is elongated and is tubular-shaped. Preferably the housing 34 is made of a material which is transparent, such as lucite, or a clear rigid pipe material of polyvinyl chloride known as EXCELON R 4000, manufactured by Thermoplastic Proceses, Inc. of Sterling, N.J., so that the sampling liquid may be viewed by an individual when it is removed from the well. The housing 34 is preferably made two to three feet long and its exact length depends upon the diameter utilized and the amount of sample liquid to be obtained and, of course, has an outer diameter which is smaller than the inner diameter of the well pipe into which it is to be inserted to obtain the sample. The upper portion of housing 34 is provided with a device for retaining a flexible line or rope 36 therein. In the preferred embodiment, this is accomplished by providing a pair of in line apertures 38 and 40 through which the rope 36 may be passed and knotted as shown just above the housing 34 thereby affixing the rope to the housing in a simple, convenient manner without utilizing any adhesives or other contaminating materials. The rope 36 is preferably passed through an aperture 42 provided in the well cap 18. Here again, a retaining device is utilized to prevent the rope from sliding back through aperture 42 and in the preferred embodiment merely consists of a knot 43 provided proximate the end of the rope 36. Thus, if by accident, the liquid sampling apparatus is dropped by the individual attempting to take a sample, it will not fall into the well and be unretrievable. The well cap being slightly larger than the well pipe and threaded therein will prevent the sampling apparatus from falling into the well with the rope 36.

When the samping apparatus is to be stored for future use, it may be raised up out of the well and aperture 30 or 32 placed over a portion 26 of the retaining device 24 provided in cover 18. Thus, it will remain proximate the well cap as the well cap is threaded onto the well topping thereby sealing the well from any foreign contaminants.

Spaced at approximately two to five inches from the lower end portion 44 of the housing 34 is a valve seat 46 formed in the housing in accordance with the manufacturing technique described hereinafter in further detail. Preferably the valve seat 46 is positioned between two and six inches (5.08–15.25 cm) from the lower edge 44 of the housing 14. Ideally, it is placed between two to three inches (5.08–7.62 cm) from the lower edge of the housing in order to avoid disturbing any contaminants appearing on the surface of the water as it is lowered into the well. The water 48 which may have a fine coating or sheen 50 floating thereon will rise into the lower opening 52 provided in the housing 34 and since lower edge 44 is provided with a chamber 54, the coating 50 is not disturbed as the housing 34 is lowered into the water 48. Therefore, the sample obtained in the samping apparatus 10 will clearly reflect what appears on the surface and in the water being sampled. The sample water with its associated contaminants will flow upwardly through valve seat 46 displacing the sphere or ball 60, preferably made of acrylic material, and fill a portion 56 of the housing 34 and is not permitted to overflow the upper edge of the housing 34. The ball 60 is provided with a specific gravity greater than water so that it may settle to the valve seat 46 when it is left in position for any length of time or is raised out of the well. The depth of sampling may readily be determined by experimentation by one experienced in obtaining such samples. An individual experienced in obtaining samples may readily discern when the sampling device has entered the water and will limit the further travel of the sampling device 10 so that the sample of liquid will not overflow the housing 34. As the liquid sampling apparatus 10 is raised out of the water the ball 60 will sink to the valve seat 46 closing aperture retaining the water in the housing 34 which then may be observed by the individual when he pulls the sampling apparatus out of the well pipe.

In operation, the liquid sampling apparatus of the instant invention is retained on the hook portion 26 of the retaining device 24 with the well cap screwed into place and the well topping 14 thereby sealing the well pipe. An individual desiring to obtain a sample of liquid in the well would remove the well cap by unthreading it from the well topping and raise it upwardly, thereby drawing the liquid sampling apparatus 10 out of the well pipe. The line or rope 36 will have been permitted to fall downwardly within the spacing bewteen the inner diameter of the well pipe and the outer diameter of the housing 34. Once the cap 18 has been removed, the liquid sampling apparatus is slowly lowered into the well until it reaches the water therebelow. Once the sampling apparatus has had sufficient time to permit the liquid to flow into the housing 34, the housing 34 is raised out of the well and may be viewed by the individual obtaining the sample or the liquid contained in the housing may be poured into another container for evaluation at a laboratory.

The construction of the valve utilized in the sampling apparatus is simple, efficient, and is effectively self-clearing, and if necessary may be cleaned by utilizing the proper cleaning materials. Restraining device 62 may be readily removed from the housing by utilizing a rod inserted from the lower edge 44 of the housing 14 and after cleaning may readily be inserted again by applying pressure to compress the walls until it is able to be received by the housing.

Figure 2:
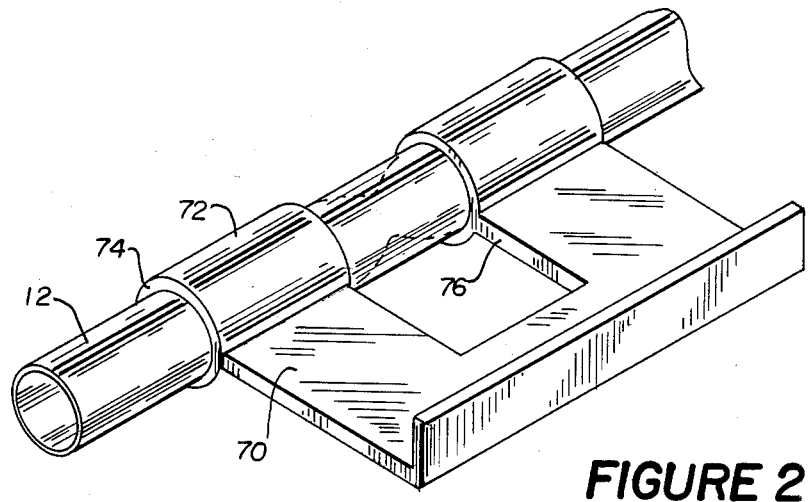
FIG. 2 is a pictorial representation of a holding jig for the housing member.
Figure 3:
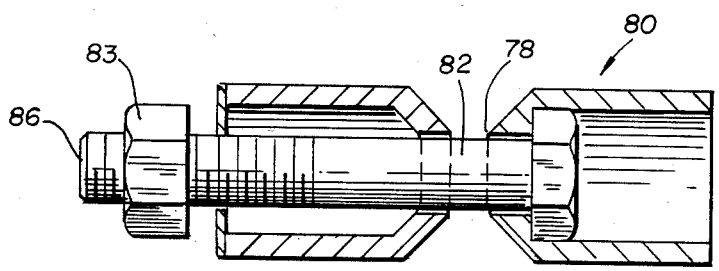
FIG. 3 is a view partially in cross-section of the separable hourglass-like fixture.
Figure 4:
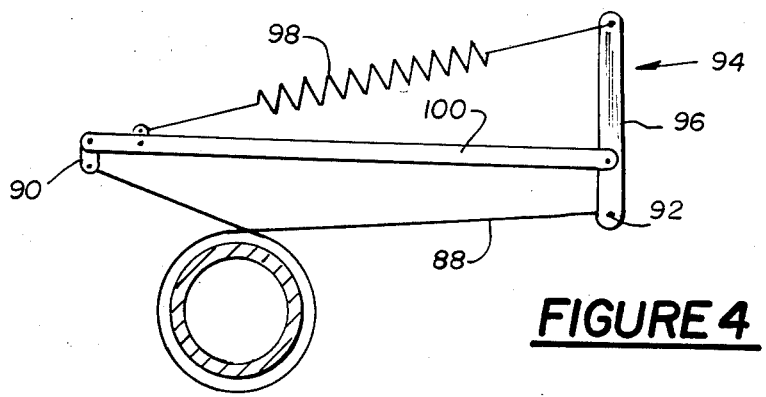
FIG. 4 is a side view in elevation of a typical holding bow utilized to shape the housing member according to the method of the present invention.

The sampling apparatus may readily be manufactured with the aid of the jigs and fixtures disclosed in FIGS. 2, 3 and 4. The housing 12 is preferably manufactured by obtaining the desired length of rigid plastic material such as EXCELON R-4000 which has one end thereof emersed in an oil bath at approximately 400° F. until the rigid material becomes malleable. The housing 12 is then removed from the oil bath, not shown, and placed in a fixture or jig 70 (FIG. 2) which may be formed from an angle iron. The distal end 72 of the jig 70 is provided with a circularly-shaped aperture 74 that is provided with an opening or cut 76 whose purpose will become apparent shortly.

A separable (two piece) hourglass-like fixture member shown in FIG. 3 is inserted into the opening of housing member 12 so that the narrow portion 78 of the fixture 80 occurs in the space 76 provided in jib 70. Bolt 82 holds both sections of the fixture 80 together and by tightening nut 84 on the threaded portion 86 of bolt 82 both sections of the fixture 80 will remain in position when inserted into the housing 12.

A flexible cord member or nylon 88 preferably $\frac{1}{8}$ inch in diameter is wrapped once around the circumference of housing 12 and connected to ring 90 on one end and 92 on the other end of holding bow 94 shown in FIG. 4. Upright arm 96 has one end of a spring 98 affixed on the distal end thereof with the other end of spring 98 affixed on arm 100 proximate ring 90 thereby maintaining line 88 with the proper tension thereon. Moving bow 94 forward and back perpendicular to the axis of housing 12 and in line with the narrow portion 78 of fixture 80 will cause the housing 12 to move inwardly and upon cooling will retain a configuration of the fixture shown in FIG. 3. The cord member 88 is removed once the housing is cooled and fixture 83 is separated by the removal of nut 83 from bolt 82 thereby allowing the fixture 80 to be removed from both ends of the housing 12. The ball 60 may then be inserted into the housing 12 from the end which was not subjected to the heating and it will be retained in position by inserting ring 62 from the same end thereafter. Preferably ring 62 is made of the same material as housing 12 and by exerting sufficient pressure thereon it will distort and be receivable into the opening of housing 12 and is preferably positioned approximately $\frac{1}{2}$ inch above the ball 60.

By providing the two inline holes 38 and 40 proximate the distal end 58 of the housing 12 the line 36 may readily be affixed thereto in a conventional manner.

Hereinbefore has been disclosed a simple, reliable liquid sampling apparatus and a method for the manufacture thereof, which may be used to obtain liquid samples from relatively narrow well piping. It will be understood that various changes of the details, materials, arrangement of parts, operating conditions, and manufacturing fixtures which have been herein described and illustrated in order to explain the nature of the invention and the method of manufacture may be made by those skilled in the art within the principles and scope of the present invention.

Having thus set forth the nature of the invention, what is claimed is:

1. A liquid sampling apparatus for use in a well pipe having a removable cap comprising:
   (a) a unitary elongated hollow housing means for insertion into said well pipe, the internal diameter of said well pipe being larger than the outer diameter of said hollow housing means, said housing means including;
      (i) retaining means disposed on one end for retaining one end of a flexible line thereon, and
      (ii) valve seat means displaced from the other end of said housing means, said valve seat means being an integral part of said housing and extending inwardly; and
   (b) spherical valve means disposed between said valve seat means and said one end of said housing means, said valve means moving freely within said housing means and adapted to cooperate with said valve seat means to retain liquids disposed between said valve seat means and said housing one end.

2. A liquid sampling apparatus according to claim 1 further including restraining means disposed within said hollow housing means between said one end and said valve seat means for preventing said spherical valve means from exiting from said housing means one end upon insertion of said housing means into said liquid for a sampling thereof.

3. A liquid sampling apparatus according to claim 1 wherein said pipe cap is provided with means for retaining the other end of said flexible line thereon and for retaining said housing means proximate thereto.

4. A liquid sampling apparatus according to claim 1 wherein said spherical valve means has a density greater than the density of said liquid to be sampled to insure cooperation between said valve seat means and said spherical valve means after said liquid has entered said housing means.

5. A liquid sampling apparatus according to claim 2 wherein said restraining means is retained within said housing means by frictional forces.

6. A liquid sampling apparatus according to claim 2 wherein said restraining means is disposed within said housing means between ¼ inch (0.635 cm) and ¾ inch (1.91 cm) above the spherical valve means when cooperating with said valve seat means.

7. A method of manufacturing a liquid sampling apparatus comprising the steps of:
(a) emersing a portion of hollow tube of rigid plastic material into a bath having a temperature above the flow point of said material;
(b) inserting said material into a jig suitable for receiving said tubular material and having an open area for exposing a small portion of said heated material;
(c) placing a separable hourglass-like fixture member into said tubular material, said fixture having an outer diameter slightly smaller than the inner diameter of said tubular material, the narrow portion of said hourglass-like fixture member being disposed within said open area of said jig;
(d) applying a flexible cord member about the circumference of said tubular member in line with said narrow portion of said hourglass-like fixture member with a holding bow means;
(e) moving said bow means back and forth perpendicular to the axis of said tubular material until said tubular material cools to room temperature;
(f) removing said separable hourglass-like fixture from said tubular member;
(g) inserting a spherical member into said tube at the end opposite said heated portion;
(h) placing a restraining means into said tubular material from the end opposite said heated portion; and
(i) forming a restraining means proximate said non-heated end of said tubular material.

8. A method of manufacturing a liquid sampling apparatus according to claim 7 further including the step of:
(j) affixing a flexible line onto said retaining means.

* * * * *